(12) United States Patent
Merz et al.

(10) Patent No.: US 11,889,978 B2
(45) Date of Patent: Feb. 6, 2024

(54) INTUBATION SYSTEM

(71) Applicant: Karl Storz SE & Co. KG, Tuttlingen (DE)

(72) Inventors: Ulrich Merz, Tuttlingen (DE); Eugenia Fuhr, Tuttlingen (DE); Toralf Popp, Schaffhausen (CH); Urs Vogel, Schaffhausen (CH)

(73) Assignee: KARL STORZ SE & CO. KG, Tuttlingen (DE)

( * ) Notice: Subject to any disclaimer, the term of this patent is extended or adjusted under 35 U.S.C. 154(b) by 350 days.

(21) Appl. No.: 17/115,406

(22) Filed: Dec. 8, 2020

(65) Prior Publication Data

US 2021/0085154 A1    Mar. 25, 2021

Related U.S. Application Data

(63) Continuation of application No. 15/606,974, filed on May 26, 2017, now Pat. No. 10,888,213.

(30) Foreign Application Priority Data

Jul. 19, 2016    (DE) .......................... 102016113318.3

(51) Int. Cl.
*A61B 1/00* (2006.01)
*A61B 1/267* (2006.01)

(52) U.S. Cl.
CPC ...... *A61B 1/00048* (2013.01); *A61B 1/00052* (2013.01); *A61B 1/267* (2013.01)

(58) Field of Classification Search
None
See application file for complete search history.

(56) References Cited

U.S. PATENT DOCUMENTS

| 9,095,298 B2 | 8/2015 | Ashcraft et al. |
| 2003/0195390 A1 * | 10/2003 | Graumann ......... A61B 1/00108 600/188 |

(Continued)

FOREIGN PATENT DOCUMENTS

CN    201328799 Y    10/2009

OTHER PUBLICATIONS

German Search Report; Application No. 10 2016 113 318.3; Completed Date: Jan. 20, 2017; dated Jan. 25, 2017; 8 Pages.

(Continued)

*Primary Examiner* — Heather R Jones
(74) *Attorney, Agent, or Firm* — Honigman LLP (57) ABSTRACT

An intubation system includes an intubation instrument for capturing an image, wherein the intubation instrument has a first interface for providing an image signal representing the captured image, a display device with a second interface for receiving the image signal, wherein the display device is provided and designed to display the image captured by the intubation instrument, and a cable with a third interface at a first end of the cable and with a fourth interface at a second end of the cable. The first, second, third, and fourth interfaces are designed such that the first interface at the intubation instrument is connectable directly to the second interface at the display device and is alternatively connectable directly to the third interface at the cable, and such that the second interface at the display device is connectable directly to the first interface at the intubation instrument and is alternatively connectable directly to the fourth interface at the cable.

2 Claims, 4 Drawing Sheets (56) References Cited

U.S. PATENT DOCUMENTS

| | | |
|---|---|---|
| 2007/0106121 A1 | 5/2007 | Yokota et al. |
| 2008/0195128 A1 | 8/2008 | Orbay et al. |
| 2011/0137127 A1 | 6/2011 | Schwartz et al. |
| 2011/0245609 A1* | 10/2011 | Laser ................. A61B 1/00052 600/109 |
| 2012/0215069 A1 | 8/2012 | Bullard |
| 2012/0316398 A1 | 12/2012 | Ashcraft et al. |
| 2013/0018227 A1* | 1/2013 | Schoonbaert ...... A61B 1/00052 600/188 |
| 2015/0112146 A1 | 4/2015 | Donaldson |
| 2015/0362828 A1* | 12/2015 | Patel ................... A61B 5/6898 348/75 |
| 2016/0128556 A1 | 5/2016 | Lai |
| 2016/0242637 A1* | 8/2016 | Tydlaska ............ A61B 1/00052 |

OTHER PUBLICATIONS

German Office Action; Application No. 10 2017 116 294.1; dated Jun. 10, 2020; 10 Pages.

U.S. Office Action; U.S. Appl. No. 15/606,974; dated Aug. 23, 2019; 6 Pages.

U.S. Office Action; U.S. Appl. No. 15/606,974; dated Dec. 12, 2019; 11 Pages.

U.S. Office Action; U.S. Appl. No. 15/606,974; dated Jun. 18, 2020; 7 Pages.

* cited by examiner

Fig. 12

INTUBATION SYSTEM

TECHNICAL FIELD

The present invention relates to an intubation system that is easy to handle even in unusual circumstances.

BACKGROUND

When intubating a patient, a clear or unobstructed view of the larynx, in particular of the vocal cords, is necessary in order to avoid endangering or injuring the patient. To this end, a laryngoscopy system or intubation system is in particular used that comprises a curved blade, a handle connected mechanically to the proximal end of the blade, and a screen connected to the proximal end of the handle. A light source illuminates the environment of the distal end of the blade. A camera captures an image of the environment of the distal end of the blade. The image is reproduced on the screen. Such a laryngoscope is described in U.S. Pat. No. 9,095,298 B2, for example.

A conventional laryngoscopy system or intubation system allows medical personnel to carry out visual monitoring during the intubation of a patient or during similar measures. However, intubation of a patient may in some circumstances be difficult or fraught with risk. In emergency medicine, for example, situations arise in which the head of a patient is not freely accessible. If spatial conditions are unfavorable, it may prove difficult to view the image on the screen. In neonatology too, intubation using a conventional laryngoscope may entail an increased risk of injury to the patient. In particular, the weight of the laryngoscope may make it considerably difficult to achieve delicate and cautious handling under the conditions that prevail in neonatology.

US 2008/0195128 A1 describes a surgical instrument for minimally invasive surgery of carpal tunnel syndrome (paragraphs [0002], [0004] to [0019]). An arm 36 at a display 54 can be connected directly to a handle 30 of the surgical instrument (paragraphs [0159], [0175]; FIG. 3A). Alternatively, the display 54 can be connected to the handle 30 by means of a cable 52 (paragraph [0175]; FIG. 1).

CN 201328799 describes a video laryngoscope having a laryngoscope 1 with a camera 104 (the paragraph bridging pages 4 and 5 of the description; FIG. 2). The video laryngoscope can be connected directly to a display 4 (FIGS. 1 and 3) or can be connected via a cable 9 to a display charging stand 10, which for its part is connectable to the display 4 (FIG. 4; second complete paragraph on page 6 of the description). For this purpose, the display 4 comprises a plug connector 2 (the paragraph bridging pages 4 and 5 of the description; FIG. 1). A damped pivot joint 3 permits pivoting of the plug connector 2 relative to the display 4 within an angle range of +95 degrees to −60 degrees (ibid.; FIG. 3).

SUMMARY

It is an object of the present invention to make available an improved intubation system.

This object is achieved by the subject matter of the independent claim.

Developments are set forth in the dependent claims.

Embodiments of the present invention are based on the idea of making available a laryngoscopy or intubation system in which a screen, a monitor or another display device can be connected to the handle of a laryngoscope or of an intubation endoscope directly or, alternatively, indirectly via a cable provided for the purpose.

An intubation system includes an intubation instrument for capturing an image, wherein the intubation instrument includes a first interface for providing an image signal representing the image, a display device with a second interface for receiving the image signal, wherein the display device is provided and designed to display the image captured by the intubation instrument, and a cable with a third interface at a first end of the cable and with a fourth interface at a second end of the cable, wherein the first interface at the intubation instrument, the second interface at the display device, the third interface and the fourth interface at the cable are designed such that the first interface at the intubation instrument is connectable directly to the second interface at the display device and is alternatively connectable directly to the third interface at the cable, and such that the second interface at the display device is connectable directly to the first interface at the intubation instrument and is alternatively connectable directly to the fourth interface at the cable.

The intubation instrument is an instrument that is suitable for facilitating or supporting visual monitoring during intubation. This does not exclude a suitability of the intubation instrument for other uses, for example for laryngoscopy without intubation.

The intubation instrument is in particular a video laryngoscope with a handle and a camera or one or more image sensors. The handle can be connected permanently to a blade, i.e. such that it is not releasable without destruction. Alternatively, the handle can be designed to be connected releasably to a blade. The blade is in particular curved or able to be curved. Alternatively, the blade can be straight or have a straight portion. The proximal end of the blade is in particular connected or connectable rigidly to the handle of the laryngoscope. A proximal area of the blade adjoins the handle in particular at an angle of between 90 degrees and 150 degrees or between 110 degrees and 130 degrees. Alternatively, the handle of the laryngoscope can be connected to the blade rectilinearly. The camera or the one or more image sensors are arranged in particular at the blade or in the handle. A light admission face, through which light can enter from the environment of the distal end of the blade, is in particular arranged near the distal end of the blade.

Alternatively, the intubation instrument is or includes an intubation endoscope with a straight or curved, rigid or flexible shaft, which can be combined with a blade or with a laryngoscope in order to form a video laryngoscope or a medical instrument having a functionality that is similar to or corresponds to the functionality of a video laryngoscope. A light admission face, through which light can enter from the environment of the distal end of the blade, is in particular arranged at or near the distal end of the intubation endoscope. The intubation endoscope in particular includes a camera or one or more image sensors near the light admission face or near the proximal end of the intubation endoscope.

If the one or more image sensors is/are spaced apart from the light admission face, a coherent bundle of optical fibers or a relay lens system can be arranged for example between the light admission face and the image sensor or the image sensors.

Moreover, the intubation instrument includes in particular a light source and/or a light exit face through which illumination light generated by a light source can exit in order to illuminate an environment of the distal end of the intubation instrument. If the intubation instrument is a laryngoscope, the light exit face is in particular arranged near the distal end of the blade. If the intubation instrument is an intubation endoscope, the light exit face is in particular arranged near the distal end of the shaft of the intubation endoscope.

The first interface is in particular arranged at the proximal end of the intubation instrument. If the intubation instrument is a laryngoscope, the first interface is in particular arranged at the proximal end of the handle and thus at the proximal end of the laryngoscope.

The first interface is in particular formed by a plug connector, for example a socket or a plug, or includes a plug connector.

The second interface of the display device is in particular formed by a plug connector corresponding to the first interface of the intubation instrument, for example a plug or a socket, or includes a plug connector.

The cable is in particular flexible, that is to say elastically and/or plastically deformable. The cable is in particular provided and designed to transmit electrical power from the display device to the intubation instrument and to transmit an analog or digital, electrical or optical image signal from the intubation instrument to the display device. Moreover, the cable is provided and designed in particular to transmit control signals in one direction or in both directions. Moreover, the cable can be provided and designed to transmit an analog or digital, electrical or optical sound signal or audio signal. In particular, the cable is provided and designed to transmit a sound signal or audio signal from the intubation instrument to the display device.

The first end of the cable is in particular the distal end, i.e. the end directed toward the intubation instrument and thus toward the patient during the intended use. The second end of the cable is in particular the proximal end, i.e. the end directed toward the display device and thus toward the medical personnel during the intended use.

The second interface at the display device and the third interface at the first end of the cable can be identical to each other or substantially similar such that both the third interface at the first end of the cable and also the second interface at the display device correspond to the first interface at the intubation instrument and can be mechanically and electrically and/or optically connected in an identical or similar way to the first interface at the intubation instrument. The first interface at the intubation instrument and the fourth interface at the second end of the cable can be identical to each other or substantially similar such that both the first interface at the intubation instrument and also the fourth interface at the second end of the cable correspond to the second interface at the display device and can be mechanically, electrically and/or optically connected in an identical or similar way to the second interface at the display device.

By virtue of the design of the interfaces, the intubation system can be used in several different configurations. If the display device is connected directly to the intubation instrument without use of the cable, a compact unit is obtained which is easy to handle and safe to use in many pre-clinical or clinical situations.

If the display device is connected to the intubation instrument indirectly, namely by means of the cable, a configuration is obtained which, in many situations in emergency medicine or in clinical practice, can simplify or indeed facilitate the handling of the intubation system or the view of the display device and therefore, for example, safe intubation of a patient. Moreover, the weight of the display device does not act on the intubation instrument if it is only connected thereto indirectly by means of the cable. This may simplify or indeed facilitate particularly delicate handling of the intubation instrument, as may be required in neonatology for example.

The intubation system facilitates both configurations and thus easily provides a degree of flexibility and adaptability to specific situations that conventional intubation systems lack.

In an intubation system as described here, the first interface at the intubation instrument, the second interface at the display device, the third interface and the fourth interface at the cable are each provided and designed in particular to transmit electrical or optical signals and to transmit electrical or optical power.

An intubation system as described here is in particular designed such that, during an intended use of the intubation system, electrical power is transmitted from the display device to the intubation instrument and an image signal is transmitted from the intubation instrument to the display device.

In the intended use of the intubation system, in particular no electrical power is transmitted from the intubation instrument to the display device, apart from the power transmission necessarily associated with each transmission of information.

In an intubation system as described here, the cable comprises in particular no power source and comprises no further interface for receiving power.

In an intubation system as described here, the cable is in particular not a charging cable and is not designed to charge an energy store of the display device.

The cable includes no charging cradle and no charging stand and no charger for the display device.

In an intubation system as described here, the display device includes in particular an energy store or a fifth interface for direct connection to an energy store.

A display device for an intubation system as described here, or for another laryngoscopy system or intubation system, includes an energy store or an interface for direct connection to an energy store.

The energy store includes in particular an accumulator or a battery or a fuel cell for storing chemical energy and for converting chemical energy to electrical energy and/or a capacitor that is able to store the entirety of the energy converted in a period of several minutes by the display device or by the entire laryngoscopy system or intubation system. The fifth interface is distinct from the second interface of the display device, which is provided and designed to connect the display device to the first interface of the intubation instrument or to the fourth interface at the second end of the cable, and in particular also differs from this.

In an intubation system as described here, the energy store is in particular provided to supply power to the intubation instrument.

In an intubation system as described here, the intubation instrument is in particular designed to draw power from the energy store of the display device or via the fifth interface of the display device.

The intubation instrument is in particular designed to draw the entire power required in the intended use of the intubation system exclusively from the energy store of the display device or via the fifth interface at the display device, i.e. from an energy store connected to the fifth interface at the display device. In this case, power is transmitted from the energy store to the intubation instrument via the fifth interface at the display device, the second interface at the display device and the first interface at the intubation instrument or via the fifth interface at the display device, the second interface at the display device, the fourth interface at the second end of the cable, the cable, the third interface at the first end of the cable and the first interface at the intubation instrument.

A supply of power to the intubation instrument through an energy store integrated in the display device or directly connected to the display device can facilitate a particularly compact design of the intubation instrument and/or a particularly low weight of the intubation instrument. This can make it easier to achieve particularly delicate handling of the intubation instrument, as is required in neonatology for example.

A display device for an intubation system as described here, or for another laryngoscopy system or intubation system, includes an image reproduction surface for displaying an image captured by means of an intubation instrument, a recess at a rear face of the display device directed away from the image reproduction surface, into which recess an energy store is insertable, an interface for coupling the display device to an intubation instrument, and a power interface in or at the recess, for connection to an energy store inserted into the recess.

In an intubation system as described here, the display device in particular includes a recess at a rear face directed away from an image reproduction surface of the display device, into which recess an energy store is insertable, wherein the fifth interface is arranged in or at the recess.

Arranging an energy store in a recess at the rear face of the display device can facilitate simple access to the energy store and, therefore, a quick exchange of the energy store.

In an intubation system as described here, the first interface at the intubation instrument, the second interface at the display device, the third interface and the fourth interface at the cable are each designed in particular as plug connectors.

In an intubation system as described here, an area of an outer surface of the intubation instrument adjoining the first interface is in particular substantially rotationally symmetrical with respect to an axis of symmetry, wherein the area of the outer surface of the intubation instrument adjoining the first interface deviates from an ideal rotational symmetry by comprising a web parallel to the axis of symmetry.

The axis of symmetry of the area of the outer surface of the intubation instrument adjoining the first interface is in particular parallel to a plug-in direction of a plugged connection to be formed by the first interface at the intubation instrument and the second interface at the display device or the third interface at the first end of the cable. The area of the outer surface of the intubation instrument adjoining the first interface comprises in particular substantially the shape of a jacket surface of a circular cylinder. The area of the outer surface of the intubation instrument adjoining the first interface comprises in particular exactly one web and is otherwise rotationally symmetrical.

In an intubation system as described here, or in a display device as described here, an area of an outer surface of the display device adjoining the second interface is in particular substantially rotationally symmetrical with respect to an axis of symmetry, wherein the area of the outer surface of the display device adjoining the second interface deviates from an ideal rotational symmetry by comprising a web parallel to the axis of symmetry.

The axis of symmetry of the area of the outer surface of the display device adjoining the second interface is in particular parallel to a plug-in direction of a plugged connection to be formed by the second interface at the display device and the first interface at the intubation instrument or the fourth interface at the second end of the cable. The area of the outer surface of the display device adjoining the second interface comprises in particular substantially the shape of a jacket surface of a circular cylinder. The area of the outer surface of the display device adjoining the second interface comprises in particular exactly one web and is otherwise rotationally symmetrical.

In an intubation system as described here, the first interface and the second interface are mechanically connectable, in particular exclusively in such a way that the webs are flush.

Two webs are flush when, in a projection parallel to the axes of symmetry, their contours are congruent or substantially congruent or are only slightly offset from each other.

In an intubation system as described here, an area of an outer surface of the first end of the cable adjoining the third interface is in particular substantially rotationally symmetrical with respect to an axis of symmetry, wherein the area of the outer surface of the first end of the cable adjoining the third interface deviates from an ideal rotational symmetry by comprising a web parallel to the axis of symmetry.

The axis of symmetry of the area of the outer surface of the first end of the cable adjoining the third interface is in particular parallel to a plug-in direction of a plugged connection to be formed by the third interface at the first end of the cable and the first interface at the intubation instrument. The area of the outer surface of the first end of the cable adjoining the third interface comprises in particular substantially the shape of a jacket surface of a circular cylinder. The area of the outer surface of the first end of the cable adjoining the third interface comprises in particular exactly one web and is otherwise rotationally symmetrical.

In an intubation system as described here, the first interface at the intubation instrument and the third interface at the first end of the cable are mechanically connectable, in particular exclusively in such a way that the webs are flush.

In an intubation system as described here, an area of an outer surface of the second end of the cable adjoining the fourth interface is in particular substantially rotationally symmetrical with respect to an axis of symmetry, wherein the area of the outer surface of the second end of the cable adjoining the fourth interface deviates from an ideal rotational symmetry by comprising a web parallel to the axis of symmetry.

The axis of symmetry of the area of the outer surface of the second end of the cable adjoining the fourth interface is in particular parallel to a plug-in direction of a plugged connection to be formed by the second interface at the display device and the fourth interface at the second end of the cable. The area of the outer surface of the second end of the cable adjoining the fourth interface comprises in particular the shape of a jacket surface of a circular cylinder. The area of the outer surface of the second end of the cable adjoining the fourth interface comprises in particular exactly one web and is otherwise rotationally symmetrical.

In an intubation system as described here, the second interface at the display device and the fourth interface at the second end of the cable are mechanically connectable, in particular exclusively in such a way that the webs are flush.

Since a mechanical connection also means that an electrical and/or optical connection of the first interface and of the second interface is possible only when the webs are flush, an incorrect connection, or a connection in an unintended orientation or configuration, is not possible. The flush arrangement of webs can be identified both visually and by touch. Thus, the webs can assist in a reliable and quick connection of the intubation instrument and of the display device even under unfavorable conditions.

In an intubation system as described here, a grip area near the second end of the cable comprises in particular a substantially ring-shaped groove, wherein the ring-shaped groove is interrupted by a web.

The groove comprises in particular a shallow cross section. The ratio between the depth of the groove and the width of the groove is in particular in a range with a lower limit of 1:20 or 1:10 and an upper limit of 1:4 or 1:6.

The ring-shaped groove is in particular interrupted by exactly one web. The web is in particular parallel to a plug-in direction of a plugged connection to be formed by the second interface at the display device and the fourth interface at the second end of the cable.

In an intubation system as described here, the web interrupting the ring-shaped groove in the grip area and the web at the area adjoining the fourth interface are in particular flush.

In an intubation system as described here, the display device comprises in particular a first component having a substantially shallow cuboid shape with cuboid edges and with an image reproduction surface, wherein the display device comprises a second component with a substantially L-shaped configuration and with a first limb and a second limb, wherein the first limb of the second component is connected to the first component in such a way that the second component is pivotable relative to the first component about a pivot axis, wherein the pivot axis is parallel to one of the cuboid edges of the first component and orthogonal to both limbs of the second component, and wherein the second interface is arranged at the second limb of the second component or is integrated therein or forms the second limb of the second component.

In an intubation system as described here, the second component of the display device is arranged in particular at a middle third of one of the cuboid edges of the first component.

The second component of the display device is in particular arranged in the middle of one of the cuboid edges of the first component.

In an intubation system as described here, a plug-in direction of the second interface is in particular parallel to the second limb of the second component.

A display device for an intubation system as described here, or for another laryngoscopy system or intubation system, includes a first component having a substantially shallow cuboid shape with cuboid edges and with an image reproduction surface, a second component with a substantially L-shaped configuration and with a first limb and a second limb, and an interface for coupling the display device to a laryngoscope or to an intubation instrument, wherein the first limb of the second component is connected to the first component in such a way that the second component is pivotable relative to the first component about a pivot axis, wherein the pivot axis is parallel to one of the cuboid edges of the first component and orthogonal to both limbs of the second component, and wherein an interface is arranged at the second limb of the second component or is integrated therein or forms the second limb of the second component.

In a display device as described here, the second component is arranged in particular in a middle third of one of the cuboid edges.

The second component is in particular arranged in the middle of one of the cuboid edges.

In a display device as described here, a plug-in direction of the interface is in particular parallel to the second limb of the second component.

The first component of the display device is substantially cuboid, particularly when it yields a cuboid which circumscribes the first component completely, or only with the exception of a few protruding details whose total volume amounts to not more than 5% of the volume of the cuboid, and which the first component fills to at least four fifths or to at least nine tenths or to at least 19 twentieths. The shape of the first component of the display device deviates from a cuboid particularly insofar as corners and edges of the first component may be rounded.

The second component of the display device is in particular arranged in the middle of one of the four longest cuboid edges or in the middle of one of the four second longest cuboid edges.

BRIEF DESCRIPTION OF THE DRAWINGS

Embodiments are explained in more detail below with reference to the attached figures, in which.

DETAILED DESCRIPTION

Figure 1:
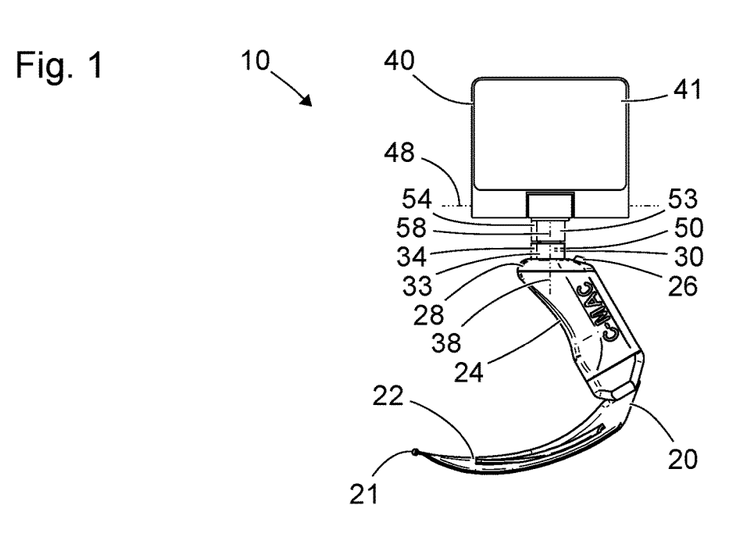
FIG. 1 shows a schematic view of a laryngoscopy system in a first configuration.

FIG. 1 shows a schematic view of a laryngoscopy system 10 with a laryngoscope 20 and a display device 40. The laryngoscopy system 10 is shown in FIG. 1 in a first configuration. The laryngoscopy system 10 is an example of an intubation system which simplifies or facilitates visual monitoring during the intubation. The laryngoscope 20 is an example of an intubation instrument. Another example of an intubation instrument, which can be part of the laryngoscopy system or intubation system 10, is an intubation endoscope with a straight or curved, rigid or flexible shaft, which can be combined with a blade or with a laryngoscope in order to form a video laryngoscope or a medical instrument with a functionality that is similar to or corresponds to the functionality of a video laryngoscope.

The laryngoscope 20 comprises a distal end 21, which is formed by a curved blade 22. The blade 22 is provided and designed to be introduced into the throat (pharynx) of a patient and there in particular to move the tongue forward and, for example, simplify or facilitate an intubation procedure. The proximal end of the blade 22 is connected to a handle 24. A push button 26 for controlling one or more functions of the laryngoscopy system 10 is provided at a proximal (in FIG. 1 upper) end 28 of the handle 24 and of the laryngoscope 20.

The laryngoscope 20 also comprises at its proximal end 28 a socket 30 serving as an interface to the display device 40. The socket 30 is a substantially concave component and is not visible in FIG. 1. Only a surface area 33 of the laryngoscope 20 adjoining the socket 30 is visible. The surface area 33 encloses the socket 30 or a part of the socket 30, which is actually able to reach deeper into the handle 24 of the laryngoscope 20.

The surface area 33 adjoining the socket 30 comprises substantially the shape of a jacket surface of a circular cylinder. The surface area 33 adjoining the socket 30 comprises a web 34, in a deviation from the shape of an ideal circular cylinder. The web 34 is parallel to an axis of symmetry 38 of the symmetrical portion of the surface area 33 of the laryngoscope 20 adjoining the socket 30.

The display device 40 comprises an image reproduction surface 41. An image captured by a camera of the laryngoscope 20 can be reproduced at the image reproduction surface 41, for example by means of a liquid crystal display or a matrix or an array of light-emitting diodes.

The display device 40 moreover comprises a plug 50 as an interface to the laryngoscope 20. The plug 50 at the display device 40 corresponds to the socket 30 at the laryngoscope 20. In the configuration shown in FIG. 1, the plug 50 of the display device 40 is arranged largely inside the socket 30 of the laryngoscope 20 and is therefore not visible.

A surface area 53 of the display device 40 adjoining the plug 50, and also visible in the configuration shown in FIG. 1, comprises substantially the shape of a jacket surface of a circular cylinder. In a deviation from the shape of an ideal circular cylinder, a web 54 is provided at the surface area 53 adjoining the plug 50. The web 54 is parallel to an axis of symmetry 58 of the symmetrical portion of the surface area 53 adjoining the plug 50.

The surface area 33 of the laryngoscope 20 adjoining the socket 30 and the surface area 53 of the display device 40 adjoining the plug 50 have the same diameters and, in the configuration shown in FIG. 1, are arranged flush and adjacent to each other. The web 34 of the surface area 33 of the laryngoscope 20 adjoining the socket 30 and the web 54 at the surface area 53 of the display device 40 adjoining the plug 50 also comprise identical or similar cross sections.

In the configuration shown in FIG. 1, the web 34 at the surface area 33 of the laryngoscope 20 adjoining the socket 30 and the web 54 at the surface area 53 of the display device 40 adjoining the plug 50 are flush. The socket 30 and the plug 50 are designed such that the intended plugged connection between the plug 50 at the display device 40 and the socket 30 at the laryngoscope 20 can only be produced when the webs 34, 54 are flush.

The intended plug-in direction of the plug 50 at the display device 40 and of the socket 30 at the laryngoscope 20 is parallel to the axis of symmetry 38 of the surface area 33 of the laryngoscope 20 adjoining the socket 30, to the axis of symmetry 58 of the surface area 53 of the display device 40 adjoining the plug 50, and to the webs 34, 54.

The laryngoscopy system 10 is shown in FIG. 1 in a configuration or situation that is suitable for many applications of the laryngoscopy system 10. By means of the plugged connection between the plug 50 at the display device 40 and the socket 30 at the laryngoscope 20, the laryngoscope 20 and the display device 40 are connected to each other mechanically and electrically. The laryngoscopy system 10 can be guided and used as a unit with one hand.

The display device 40 has two hinges, one of which facilitates a pivoting of the image reproduction surface 41 relative to the plug 50 and to the laryngoscope 20 about a horizontal pivot axis 48 in FIG. 1, and the other of which facilitates a pivoting movement of the image reproduction surface 41 about a pivot axis corresponding to the axes of symmetry 38, 58.

Figure 2:
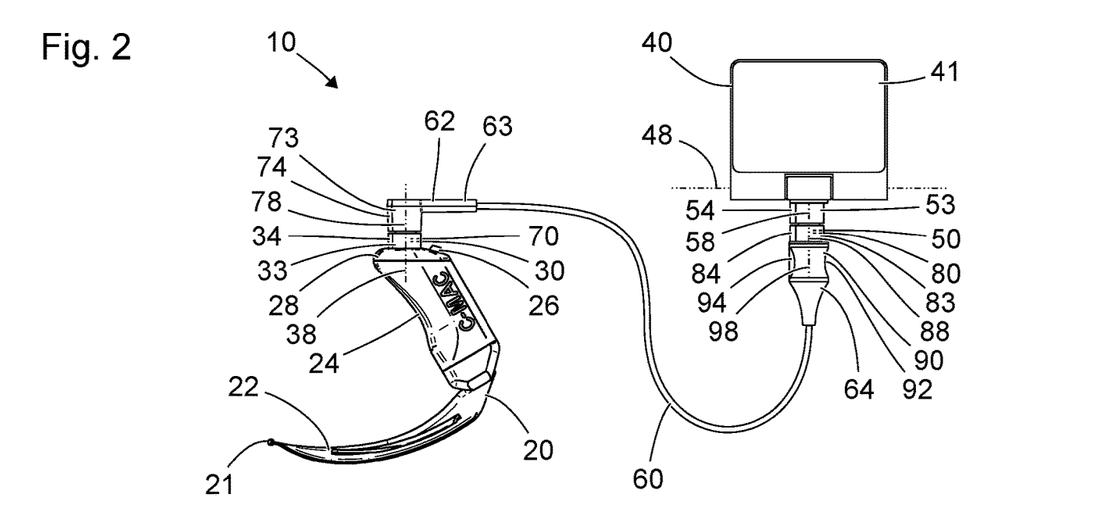
FIG. 2 shows a schematic view of the laryngoscopy system from FIG. 1 in a second configuration.

FIG. 2 shows a schematic view of the laryngoscopy system 10 from FIG. 1 in a further configuration or situation. In the situation shown in FIG. 2, the display device 40 is not connected directly to the laryngoscope. Instead, the display device 40 is connected to the laryngoscope 20 by a cable 60. The cable 60 is a constituent part of the laryngoscopy system 10.

The cable 60 comprises a first or distal end 62, which is provided and designed for connection to the laryngoscope 20, and a second or proximal end 64, which is provided and designed for releasable connection to the display device 40. Near the distal end 62 of the cable 60, an anti-kink grommet 63 is provided for protecting the cable 60 from a mechanical overload. In a deviation from the view in FIG. 2, an anti-kink grommet can also be provided at the proximal end of the cable 60.

A plug 70 serving as interface to the laryngoscope 20 and corresponding to the socket 30 at the laryngoscope 20 is provided at the distal end 62 of the cable 60, which plug 70, in the configuration shown in FIG. 2, is arranged in the socket 30 and is therefore not visible. The plug 70 at the distal end 62 of the cable 60 is identical or largely similar to the plug 50 at the display device 40. A surface area 73 of the distal end 62 of the cable 60 adjoining the plug 70 is also identical or similar to the surface area 53 of the display device 40 adjoining the plug 50. In particular, the surface area 73 of the distal end 62 of the cable 60 adjoining the plug 70 comprises substantially the shape of a jacket surface of a circular cylinder and, in a deviation from the shape of an ideal circular cylinder, comprises a web 74. The web 74 is parallel to an axis of symmetry 78 of the symmetrical portion of the surface area 73 of the distal end 62 of the cable 60 adjoining the plug 70.

A socket 80 serving as interface to the display device 40 and corresponding to the plug 50 at the display device 40 is provided at the proximal end 64 of the cable 60. The socket 80 is a substantially concave component and is not visible in FIG. 2. The socket 80 at the proximal end 64 of the cable 60 is identical or largely similar to the socket 30 at the laryngoscope 20. A surface area 83 of the proximal end 64 of the cable 60 adjoining the socket 80 is also identical or similar to the surface area 33 of the laryngoscope 20 adjoining the socket 80. In particular, the surface area 83 of the proximal end 64 of the cable 60 adjoining the socket 80 comprises substantially the shape of a jacket surface of a circular cylinder and, in a deviation from the shape of an ideal circular cylinder, comprises a web 84. The web 84 is parallel to an axis of symmetry 88 of the symmetrical portion of the surface area 83 of the proximal end 64 of the cable 60 adjoining the socket 80.

A grip area 90 is also provided at the proximal end 64 of the cable 60. The grip area 90 is immediately distal to the surface area 83 of the cable 60 adjoining the socket 80. The grip area 90 is substantially rotationally symmetrical to an axis of symmetry 98, which corresponds to the axis of symmetry 88 of the surface area 83 adjoining the socket 80.

The grip area 90 includes a substantially circular groove 92, which is interrupted by a web 94. The groove comprises a cross section with a circular arc-shaped edge and with a depth amounting to approximately one eighth of its width. The web 94 is parallel to the axis of symmetry 98 of the grip area 90. The web 94 of the grip area 90 and the web 84 at the surface area 83 of the proximal end 64 of the cable 60 adjoining the socket 80 are flush.

The webs 34, 54, 74, 84, 94 make it easier to correctly produce the plugged connections of the laryngoscopy system 10.

The configuration of the laryngoscopy system 10 shown in FIG. 2 may be particularly suitable for situations in which access to the patient is difficult, for example in emergency medicine. The display device 40 can be arranged at a suitable location independently of the position of the head of the patient. Moreover, the configuration of the laryngoscopy system 10 shown in FIG. 2 may be particularly suitable for uses in neonatology. The weight of the display device 40 does not place a load on the laryngoscope 20. This can facilitate delicate movement of the laryngoscope 20.

Figure 3:
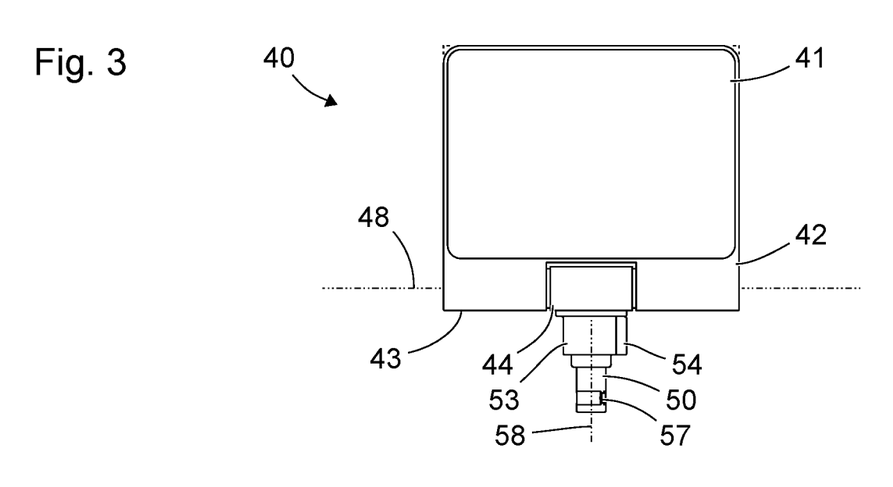
FIG. 3 shows a schematic view of a display device of the laryngoscopy system from FIGS. 1 and 2.

FIG. 3 shows a schematic view of the display device 40 of the laryngoscopy system shown in FIGS. 1 and 2. The display device 40 includes a first, substantially cuboid component 42 and a second, substantially L-shaped component 44.

Deviating from the shape of an ideal cuboid, the first component 42 comprises several rounded corners and edges. Two rounded corners can be seen at the top in FIG. 3. The contour of the cuboid, which is substantially the shape presented by the first component 42, is indicated by broken lines in the area of the rounded corners.

The cuboid, which is approximately the shape presented by the first component 42, comprises three groups of in each case four parallel cuboid edges of equal length. The cuboid edges of the group of the longest cuboid edges are parallel to the pivot axis 48. The first component 42 and the second component 44 of the display device 40 are mechanically connected to each other in such a way that the first component 42 is pivotable relative to the second component 44 about the pivot axis 48. The axis of symmetry 58 of the surface area 53 of the display device 40 adjoining the plug 50 is orthogonal to the pivot axis 48. The end of the second component 44 connected in a hinged manner to the first component 42 is arranged close to two cuboid edges 43 (which are congruent in the view in FIG. 3) and their centers.

A nose 57 at the plug 50 is visible in FIG. 3. The plug 50 comprises two noses 57, one of which is concealed and is therefore not visible in FIG. 3. In the configuration shown in FIG. 3, both noses 57 are arranged with mirror symmetry in relation to a plane that is parallel to the drawing plane of FIG. 3 and that contains the axis of symmetry 58. The noses 57 are provided, designed and arranged to engage in corresponding recesses in the socket 30 at the proximal end 28 of the laryngoscope 20 (cf. FIG. 2) when the plug 50 is in the intended orientation relative to the socket 30. In a relative orientation other than the intended one, the noses 57 positively prevent the production of a plugged connection.

Figure 4:
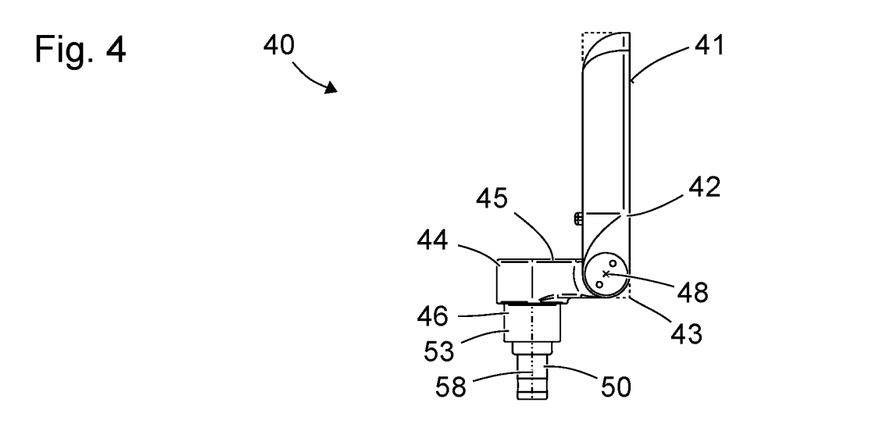
FIG. 4 shows a further schematic view of the display device from FIG. 3.

FIG. 4 shows a further schematic view of the display device 40 from FIG. 3. The drawing plane of FIG. 4 is orthogonal to the pivot axis 48, parallel to the axis of symmetry 58 of the surface area 53 of the display device 40 adjoining the plug 50, orthogonal to the plane in which the image reproduction surface 41 lies, and orthogonal to the drawing plane of FIG. 3.

Rounded edges of the first component 42 can be seen in FIG. 4. Broken lines in the area of rounded edges indicate the contour of the cuboid, which is the shape approximately presented by the first component 42.

The second component 44 is substantially L-shaped with a first limb 45 and a second limb 46. The limbs 45, 46 of the substantially L-shaped second component 44 are arranged orthogonally with respect to each other. The end of the first limb 45 of the second component 44 directed away from the second limb 46 is connected to the first component 42 in a hinged manner. The end of the second limb 46 of the second component 44 directed away from the first limb 45 is formed by the plug 50 of the display device 40.

Figure 5:
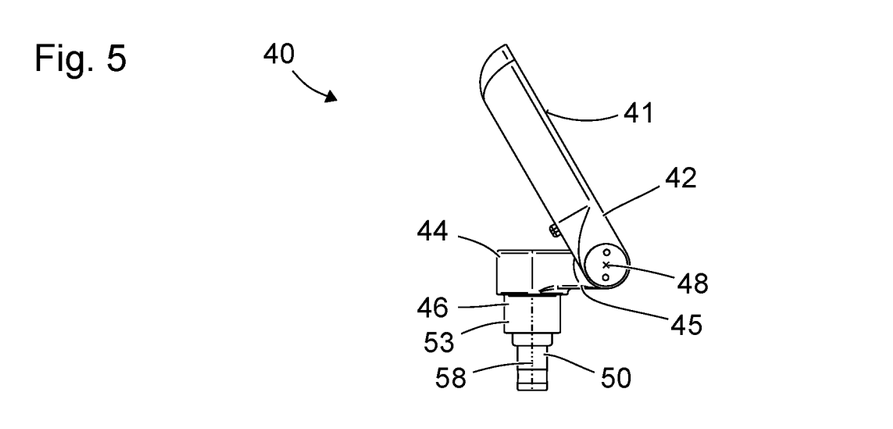
FIG. 5 shows a further schematic view of the display device from FIGS. 3 and 4.

FIG. 5 shows a further schematic view of the display device 40 from FIGS. 3 and 4. The drawing plane of FIG. 5 corresponds to the drawing plane of FIG. 4.

The display device 40 is shown in FIG. 5 in a configuration that differs from the configuration shown in FIG. 4. In particular, the first component 42 is pivoted relative to the second component 44 about the pivot axis 48, in order to facilitate an unrestricted view of the image reproduction surface 41 from another direction.

Figure 6:
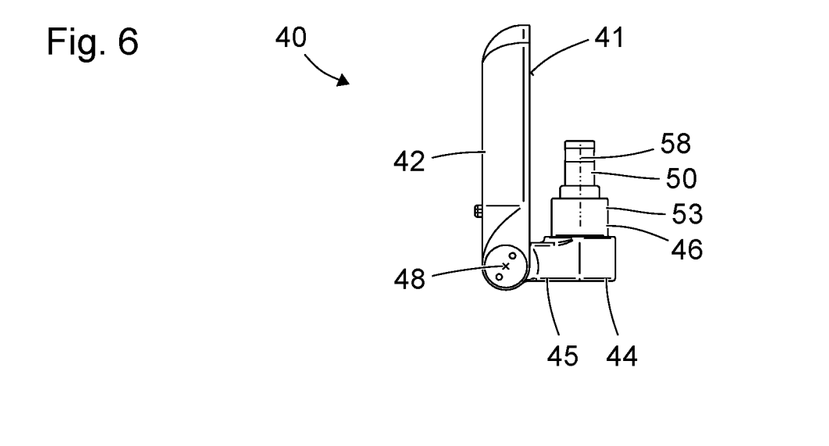
FIG. 6 shows a further schematic view of the display device from FIGS. 3 to 5.

FIG. 6 shows a further schematic view of the display device 40 from FIGS. 3 to 5. The drawing plane of FIG. 6 corresponds to the drawing planes of FIGS. 4 and 5.

The display device 40 is shown in FIG. 6 in a configuration that differs from the configurations shown in FIGS. 3 to 5. The first component 42 and the second component 44 of the display device 40 assume a third angle position relative to each other, which differs from the configurations shown in FIGS. 3 to 5. Proceeding from the configuration shown in FIGS. 3 and 4, the second component 44 is pivoted relative to the first component 42 about the pivot axis 48 by an angle of ca. 180 degrees.

Particularly when the display device 40 is connected to the laryngoscope 20, as shown in FIG. 1, or to the proximal end 62 of the cable 60, as shown in FIG. 2, the configuration shown in FIG. 6 does not facilitate a clear view of the image reproduction surface 41 of the display device 40. However, in the configuration shown in FIG. 6, the display device 40 takes up a relatively small space. The configuration shown in FIG. 6 is therefore suitable in particular for a non-operational state of the laryngoscopy system 10. When the display device 40 in the configuration shown in FIG. 6 is connected directly to the laryngoscope 20 as shown in FIG. 1, the first component 42 of the display device 40 is arranged parallel to and near the handle 24 of the laryngoscope 20.

The laryngoscopy system 10, in particular the display device 40, can be designed such that, in the configuration shown in FIG. 6, supply of power to the laryngoscopy system 10 is automatically stopped or the laryngoscopy system 10 is set to a non-operational state.

Figure 7:
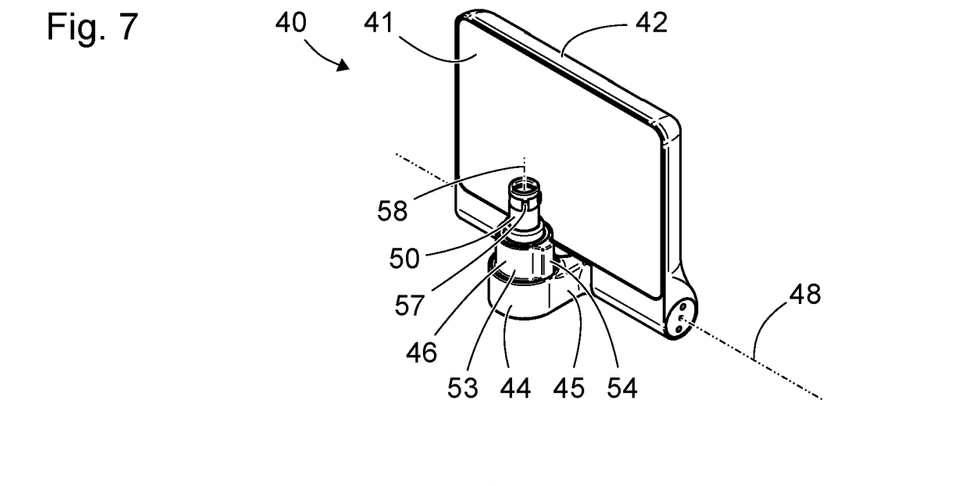
FIG. 7 shows a schematic axonometric view of the display device from FIGS. 3 to 5.

FIG. 7 shows a schematic axonometric view of the display device 40 from FIGS. 3 to 6. The configuration of the display device 40 shown in FIG. 7 corresponds to the configuration shown in FIG. 6.

Figure 8:
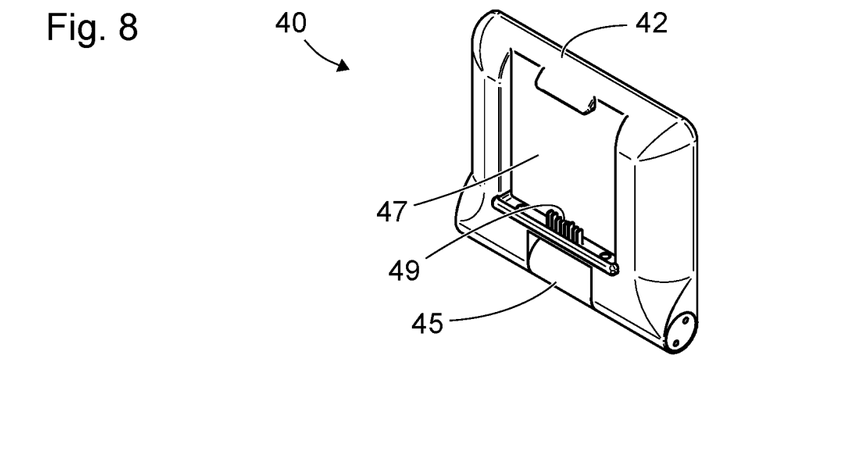
FIG. 8 shows a schematic axonometric view of the display device from FIGS. 3 to 5.

FIG. 8 shows a further axonometric view of the display device 40 shown in FIGS. 3 to 7. The configuration of the display device 40 shown in FIG. 8 corresponds to the configuration shown in FIGS. 6 and 7.

A rear face of the first component 42 of the display device 40, directed away from the image reproduction surface 41 (cf. FIGS. 3 to 7), is visible in FIG. 8. A recess 47 for receiving an accumulator for supplying power to the laryngoscopy system is provided in this rear face. An accumulator interface 49 with a plurality of electrical contacts is arranged in the recess 47.

Figure 9:
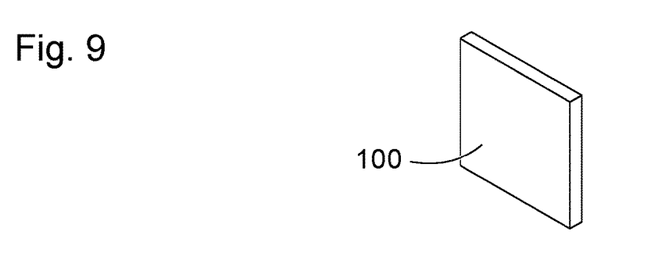
FIG. 9 shows a schematic axonometric view of an accumulator for the laryngoscopy system from FIGS. 1 and 2.

FIG. 9 shows a schematic axonometric view of an accumulator 100 for supplying power to the laryngoscopy system 10 shown in FIGS. 1 to 8. The accumulator 100 is provided and designed to be inserted into the recess 47 at the rear face of the first component 42 of the display device 40 directed away from the image reproduction surface 41 (cf. FIG. 8) and thus to be connected to the accumulator interface 49.

The accumulator 100 is provided and designed to serve as the sole energy store and sole source of electrical power for the entire laryngoscopy system 10, in particular for the display device 40 and the laryngoscope 20 with one or more light sources and/or cameras arranged therein.

In a departure from the view in FIGS. 8 and 9, the accumulator 100 can be integrated in the display device 40 such that it cannot be exchanged or cannot readily be exchanged. In particular, the accumulator 100 can be arranged inside a housing of the display device 40.

Figure 10:
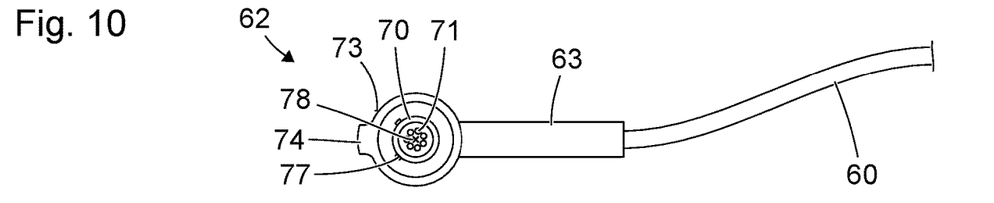
FIG. 10 shows a schematic view of a plug at a first end of the cable of the laryngoscopy system from FIGS. 1 and 2.

FIG. 10 shows a schematic view of the distal end 62 of the cable 60 shown in FIG. 2. The drawing plane of FIG. 10 is orthogonal to the plug-in direction and axis of symmetry 78 of the surface area 73 adjoining the plug 70.

The plug 70 includes several electrical contacts 71, which correspond to contacts in the socket 30 at the laryngoscope 20.

Two noses 77 are arranged at the outside of the plug 70. The noses 77 at the plug 70 at the distal end 62 of the cable 60 correspond to the noses 57 at the plug 50 at the display device 40. The noses 77 are provided, designed and arranged to engage in corresponding recesses in the socket 30 at the proximal end 28 of the laryngoscope 20 (cf. FIG. 2) when the plug 70 is in the intended orientation relative to the socket 30. In a relative orientation other than the intended one, the noses 77 positively prevent the production of a plugged connection.

The web 74, which interrupts the rotational symmetry of the surface area 73 of the distal end 62 of the cable 60 adjoining the plug 70, is so wide that it can be easily identified not just by touch but also visually. The flanks of the web 74 merge smoothly with concave fillets into the rotationally symmetrical portion of the surface area 73 of the distal end 62 of the cable 60 adjoining the plug 70.

The anti-kink grommet 63 is arranged exactly opposite the web 74, at a side directed away from the web 74.

Figure 11:
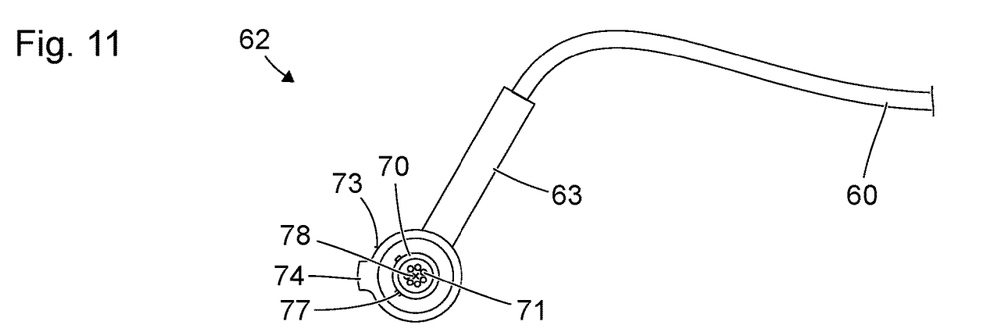
FIG. 11 shows a schematic view of a variant of the plug from FIG. 10.

FIG. 11 shows a schematic view of a variant of the distal end 62 of the cable 60 shown in FIG. 10. The nature of the view corresponds to that of FIG. 10. The variant shown in FIG. 11 differs from that shown in FIG. 10 in that the groove 74 and the anti-kink grommet 63 are not arranged exactly opposite each other. In relation to the axis of symmetry 78, the web 74 and the anti-kink grommet 63 are arranged at an angle of ca. 120 degrees.

Figure 12:
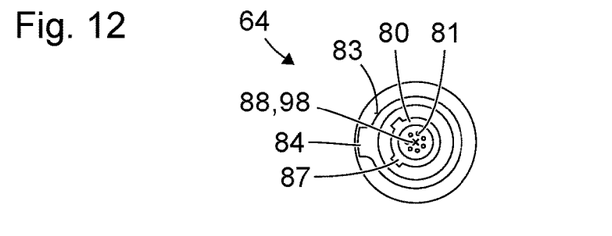
FIG. 12 shows a schematic view of a plug at a second end of the cable of the laryngoscopy system from FIGS. 1 and 2.

FIG. 12 shows a schematic view of the proximal end 64 of the cable 60 of the laryngoscopy system 10 shown in FIGS. 1 and 2. The nature of the view corresponds to that of FIGS. 10 and 11. The drawing plane of FIG. 12 is orthogonal to the axis of symmetry 88 of the surface area 83 adjoining the socket 80 at the proximal end 64 of the cable 60 and orthogonal to the axis of symmetry 98 of the grip area 90.

The socket 80 includes several electrical contacts 81, which correspond to contacts in the plug 50 at the display device 40.

Two recesses 87 in the form of two grooves extending parallel to the plug-in direction and to the axes of symmetry 88, 98 are provided in the socket 80. The recesses 87 correspond to the noses 57 at the plug 50 at the display device 40 (cf. FIG. 3). The noses 57 at the plug 50 at the display device 40 and the recesses 87 at the socket 80 at the proximal end 64 of the cable 60 ensure that a plugged connection between the plug 50 at the display device 40 and the socket 80 at the proximal end 64 of the cable 60 can be produced only in the intended manner, particularly only in the intended relative orientation.

What is claimed is:

1. A display device for a laryngoscopy system or intubation system, comprising:
   a battery supplying power to the display device and the laryngoscopy system or intubation system;
   a housing having an image reproduction surface and a rear surface opposite of the image reproduction surface, the image reproduction surface configured to display an image captured by an intubation instrument or a laryngoscope, wherein the rear surface includes a recess configured to receive a peripheral side of the battery so as to seat the battery within the recess;
   an interface for coupling the housing to one of the laryngoscope and the intubation instrument, the interface disposed on a bottom surface of the housing; and
   a power interface spaced apart from the interface, the power interface disposed on an exterior surface of the rear surface and within the recess, the power interface configured to electrically connect with the battery when the battery is disposed within the recess and an exterior surface of the battery is exposed when the battery is connected to the power interface.

2. The display device of claim 1, wherein the display device is configured to receive an image signal from the laryngoscope or intubation instrument.

* * * * *